| United States Patent [19] | [11] Patent Number: 4,967,732 |
|---|---|
| Inoue | [45] Date of Patent: Nov. 6, 1990 |

[54] ENDOSCOPE

[75] Inventor: Masahiro Inoue, Tokyo, Japan

[73] Assignee: Kabushiki Kaisha Machida Seisakusho, Tokyo, Japan

[21] Appl. No.: 509,769

[22] Filed: Apr. 17, 1990

[30] Foreign Application Priority Data

May 1, 1989 [JP] Japan ............................... 1-50262[U]

[51] Int. Cl.⁵ .............................................. A61B 1/00
[52] U.S. Cl. ...................................................... 128/4
[58] Field of Search .............................................. 128/4

[56] References Cited

U.S. PATENT DOCUMENTS

| 4,690,131 | 9/1987 | Lyddy, Jr. et al. | 128/4 |
| 4,748,969 | 6/1988 | Wardle | 128/4 |

FOREIGN PATENT DOCUMENTS

| 51-53789 | 4/1976 | Japan . |
| 55-66342 | 5/1980 | Japan . |
| 59-36 | 1/1984 | Japan . |
| 59-40002 | 11/1984 | Japan . |
| 60-177801 | 11/1985 | Japan . |
| 61-133001 | 8/1986 | Japan . |
| 62-18102 | 2/1987 | Japan . |
| 63-92603 | 6/1988 | Japan . |

*Primary Examiner*—William H. Grieb
*Attorney, Agent, or Firm*—Wegner & Bretschneider

[57] ABSTRACT

An endoscope includes a guide tube assembly for guiding an elongated treatment instrument. The guide tube assembly includes a resin tube whose internal bore serves as a guide channel for the passage of the treatment instrument therethrough. A reinforcement coil is received in a spiral groove formed in the outer peripheral surface of the resin tube. The guide tube assembly further includes a braid tube woven of yarns having low expansion properties. The braid tube covers the resin tube generally over an entire length of the resin tube. The opposite ends of the braid tube are fixed to the oppositre ends of the resin tube, respectively.

6 Claims, 2 Drawing Sheets

ENDOSCOPE

BACKGROUND OF THE INVENTION

The invention relates to an endoscope provided with a guide tube assembly for guiding a treatment instrument such as a forceps.

As is well known, an endoscope comprises a body, and a flexible insertion tube extending from the body. The distal end portion of the insertion tube is formed as a bendable portion. A rigid member, having an inspection window and an illumination window, is attached to the distal end of the bendable portion. When the flexible insertion tube is to be inserted into a body cavity, the insertion tube is bent in accordance with the configuration of the body cavity, and the bendable portion is bent by a remote control through a manipulation member mounted on the body.

The endoscope is provided with a guide means for guiding an elongated treatment instrument such as a forceps. The guide means has an inlet formed at the body, an outlet formed at the rigid member, and a guide tube assembly constituting a guide channel interconnecting the inlet and the outlet. The treatment instrument is inserted into the guide channel via the inlet, and is passed through the guide channel and the outlet, and is directed toward the body cavity. While observing the body cavity by the endoscope, the inner surface of the body cavity is treated by the treatment instrument.

A guide tube assembly shown in FIG. 2 of Japanese Laid-Open (Kokai) Utility Model Application No. 18102/87 comprises a resin tube, and the internal bore of the resin tube serves as a guide channel. A spiral groove is formed in the outer peripheral surface of the rein tube, and a reinforcement coil of steel is received in the spiral groove. Because of the provision of the spiral groove, the resin tube is considerably flexible. The reinforcement coil serves to prevent the resin tube from being deformed or crushed radially when the resin tube is bent. Since the reinforcement coil per se is flexible so as to be bent longitudinally, that is, in the direction of bending of the guide tube assembly, the reinforcement coil will not affect the flexibility of the resin tube. However, there is a possibility that the reinforcement coil may become disengaged or dislodged from the spiral groove.

In a guide tube assembly shown in FIG. 1 of the above Japanese Laid-Open Utility Model Application No. 18102/87, a resin for retaining purpose is filled in the spiral groove in the resin tube to thereby prevent the reinforcement coil from becoming disengaged from the spiral groove. However, the use of such retaining resin lowers the flexibility of the guide tube assembly.

Furthermore, in the above two guide tube assemblies, the resin tube and the reinforcement coil (as well as the retaining resin in the latter type) are considerably axially expansible. Therefore, as a result of a repeated bending of the guide tube assembly caused when bending the bendable portion of the endoscope, there is encountered a problem that the guide tube assembly remains expanded axially. The guide tube assembly, when thus expanded axially, is loosened within the insertion portion or the bendable portion, which results in a problem that the front end of the treatment instrument may be caught by the inner surface of the resin tube. This not only prevents a smooth guiding of the treatment instrument, but also may damage the resin tube.

Japanese Laid-Open Patent Application No. 66342/80, Japanese Laid-Open Utility Model Application No. 133001/86 and Japanese Utility Model Publication No. 40002/84 disclose guide tube assemblies similar to the above-mentioned guide tube assemblies.

Japanese Laid-Open Utility Model Application Nos. 53789/76, 177801/85 and 92603/88 disclose structures in which opposite ends of a guide tube are connected to a body and a rigid member, respectively.

Japanese Laid-Open Patent Application No. 36/84 discloses a braid tube woven of a metal wire and a resin yarn. The braid tube constitutes an insertion tube of an endoscope to be inserted into a body cavity.

SUMMARY OF THE INVENTION

It is an object of this invention to provide an endoscope provided with a guide tube assembly which is sufficiently flexible, and is restrained in axial expansion.

According to the present invention, there is provided an endoscope comprising:

(a) a body having an inlet for an elongated treatment instrument;

(b) a flexible insertion tube extending from the body;

(c) a rigid member mounted on a distal end of the insertion tube remote from the body, the rigid member having an outlet for the treatment instrument; and (d) a guide tube assembly for guiding the treatment instrument, the guide tube assembly being received in the body and the insertion tube and comprising (i) a resin tube whose internal bore serves as a guide channel for the passage of the treatment instrument therethrough, the guide channel interconnecting the inlet of the body and the outlet of the rigid member, the resin tube having a spiral groove formed in an outer peripheral surface thereof, (ii) a reinforcement coil received in the spiral groove in the resin tube, and (iii) a braid tube woven of yarns having low expansion properties, the braid tube being covering the resin tube generally over an entire length of the resin tube, and opposite ends of the braid tube being fixed to opposite ends of the resin tube, respectively.

DESCRIPTION OF THE PREFERRED EMBODIMENTS OF THE INVENTION

The invention will now be described with reference to the drawings.

Figure 1:
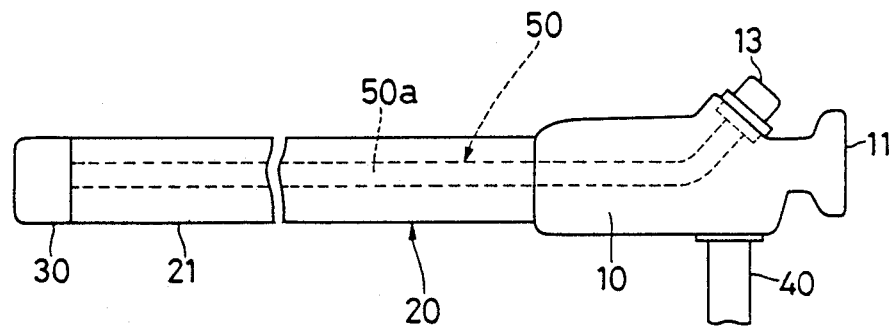
FIG. 1 is a schematic front-elevational view of an endoscope provided in accordance with the present invention.

A medical endoscope shown in FIG. 1 comprises a hollow body 10, a flexible insertion tube 20 extending longitudinally from a front face (left end face in FIG. 1)

of the body 10, and a rigid member 30 mounted on the distal end of the insertion tube 20.

The insertion tube 20 is designed to be inserted into a body cavity. The distal portion of the insertion tube 20 extending rearwardly from the rigid member 30 over a predetermined distance serves as a bendable portion 21. The bendable portion 21 differs in structure from the remainder of the insertion tube 20. A manipulation member (not shown) such as a manipulation lever is mounted on the body 10, and a manipulation force of the manipulation member is transmitted to the bendable portion 21 via a wire so as to bend the bendable portion 21.

The rigid member 30 has an inspection window and an illumination window both of which are not shown. A cable 40 extends from the side of the body 10, and a connector is attached to the distal end of the cable 40. This connector is connected to a light source device (not shown), and in this condition light from the light source device is transmitted through a bundle of optical fibers, received in the connector, the cable 40, the body 10 and the insertion tube 20, and is applied into the body cavity via the illumination window. An ocular portion 11 is formed at the rear end of the body 11, and is optically connected to the inspection window through an image-transmitting optical system (not shown) including a bundle of optical fibers. Therefore, the interior of the body cavity can be observed from the ocular portion 11.

The above construction is well known in the art, and does not constitute any important feature of the prevent invention, and therefore a detailed explanation thereof is omitted here.

The endoscope is provided with a guide means for guiding an elongated treatment instrument such as a forceps. This guide means will now be described in detail.

Figure 2:
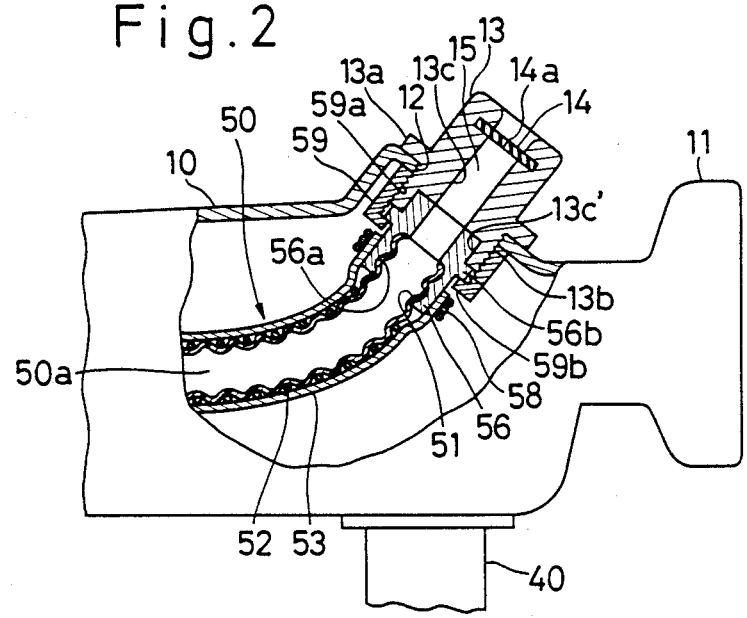
FIG. 2 is an enlarged, partly cross-sectional view of a portion of the endoscope, showing a connection between a body and a guide tube assembly.

As shown in FIG. 2, a threaded hole 12 is formed in the body 10, and a fitting 13 of a cylindrical shape is threaded into the threaded hole 12 to be fixed to the body 10. A flange 13a is formed on the outer peripheral surface of the fitting 13 intermediate the opposite ends of the fitting 13, the flange 13a being abutted against the outer surface of the body 10. A threaded portion 13b is formed on that portion of the outer peripheral surface of the fitting 13 extending between one or inner end of the fitting 13 and the flange 13a, the threaded portion 13b being threadedly engaged with the threaded hole 12.

The fitting 13 has a central bore 13c extending axially therethrough. The bore 13c is greater in diameter at its inner end portion 13c', and the remainder of the bore 13c serves as an inlet 15 for the passage of the forceps therethrough. A cover 14 of rubber is mounted on the inner peripheral surface of the inlet 15. For example, a cross-shaped slit 14a is formed in the cover 14. The cover 14 closes the inlet 15, and allows the passage of the forceps because of the provision of the slit 14a.

Figure 3:
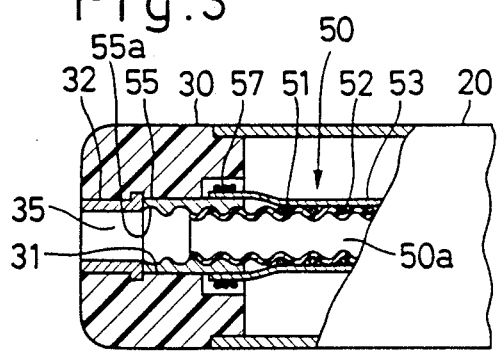
FIG. 3 is an enlarged, partly cross-sectional view of a portion of the endoscope, showing a connection between a rigid member and the guide tube assembly.

As shown in FIG. 3, the rigid member 30 has a central bore 31 extending axially therethrough, and a hollow cylindrical member 35 is embedded in the inner peripheral surface of the distal portion of the bore 31. The cylindrical member 32 constitutes an outlet 35 for the forceps.

Figure 4:
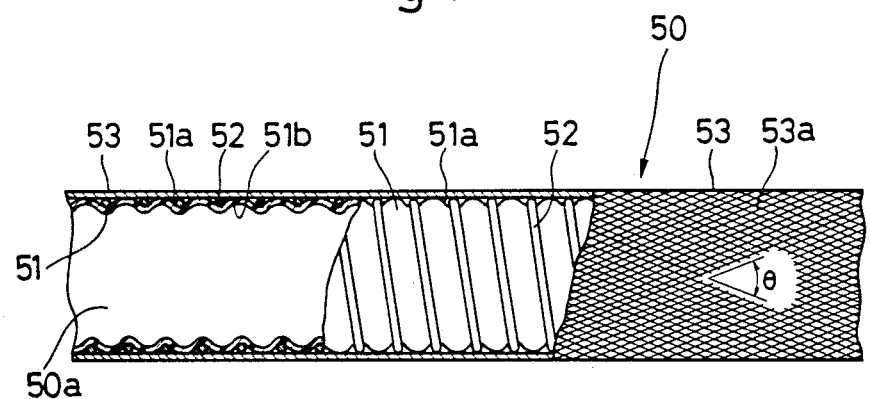
FIG. 4 is an enlarged, cross-sectional view of a portion of the guide tube assembly.

The guide means for the forceps further comprises a guide tube assembly 50. The guide tube assembly 50 is received in the body 10 and the insertion tube 20. As shown in FIG. 4, the guide tube assembly 50 comprises a resin tube 51, a reinforcement coil 52, and a braid tube 53.

The internal bore of the resin tube 51 serves as a guide channel 50a for the passage of the forceps therethrough. The inlet 15 and the outlet 35 are interconnected by the guide channel 50a. A spiral groove 51a is formed in the outer peripheral surface of the resin tube 51 over the entire length thereof. A spiral groove 51b is also formed in the inner peripheral surface of the resin tube 51, and each turn of the spiral groove 51b is disposed between respective two adjacent turns of the spiral groove 51a. Therefore, the peripheral wall of the resin tube 51 has a corrugated cross-section, and has a generally uniform thickness throughout the entire length of the resin tube 51. The inner spiral groove 51b may be omitted.

The reinforcement coil 52 is made, for example, of a steel wire, and is received in the outer spiral groove 51a in the resin tube 51 over the entire length of the resin tube 51.

The braid tube 53 is composed of yarns 53a made of a fiber having almost no or very low expansion properties, such as an aromatic polyamide fiber. The braid tube 53 covers the resin tube 51 and the reinforcement coil 52 substantially over the entire length thereof. The braid tube 53 is held in intimate contact with the resin tube 51 and the reinforcement coil 52.

The guide tube assembly 50 has a pair of connectors 55 and 56 secured respectively to the opposite ends thereof. As shown in FIG. 3, the distal connector 55 has a tubular shape, and an internally-threaded portion 55a is formed on the inner peripheral surface of the connector 55. The distal end portion of the resin tube 51 is threaded into the connector 55, and fixedly secured thereto by an adhesive or the like. The distal end portion of the braid tube 53 is fitted on the outer peripheral surface of the rear portion of the connector 55, and is fixed thereto by a thread 57 tied around the distal end portion of the braid tube 53.

As shown in FIG. 2, the proximal connector 56 has a tubular shape, and an internally-threaded portion 56a is formed on the inner peripheral surface of the front portion of the connector 56. A flange 56b is formed on the outer peripheral surface of the connector 56 intermediate the opposite ends thereof. The proximal end portion of the resin tube 51 is threaded into the internally-threaded portion 56a of the connector 56 and is fixed thereto by an adhesive or the like. The proximal end portion of the braid tube 53 is fitted on the outer peripheral surface of the front portion of the connector 56, and is fixed thereto by a thread 58 tied around the proximal end portion of the braid tube 53.

A method of assembling the guide tube assembly 50 will now be described. First, the reinforcement coil 52 is received in the spiral groove 51a in the resin tube 51, and the two connectors 55 and 56 are attached to the opposite ends of the resin tube 51, respectively. Then, the resin tube 51 is inserted into the braid tube 53. The inner diameter of the braid tube 53 is slightly greater than the outer diameter of the resin tube 51. Then, the opposite ends of the braid tube 53 are grasped by the hands or suitable jigs, and the braid tube 53 is expanded longitudinally as much as possible. As a result, the helix angle of each yarn 53a of the braid tube 53 with respect to the axis of the braid tube 53 is decreased, so that the angle $\theta$ of intersection between any two yarns 53a which are helical in opposite directions, respectively, becomes smaller. At the same time, the braid tube 53 is reduced in diameter to be brought into intimate contact with the resin tube 51 and the reinforcement coil 52. Since the reduction of the diameter of the braid tube 53 is resisted by the reinforcement coil 52, the braid tube 53 can no longer be expanded longitudinally after the braid tube 53 is brought into intimate contact with the reinforcement coil 52. Therefore, in this intimate contact condition, the intersection angle $\theta$ is the minimum, and in this condition the opposite ends of the braid tube 53 are fixed to the connectors 55 and 56, respectively.

The opposite ends of the guide tube assembly 50 are fixedly secured to the fitting 13 of the body 10 and the rigid member 30, respectively. More specifically, the connector 55 attached to the distal end of the guide tube assembly 50 is fitted in the rear portion of the central bore 31 of the rigid member 30 and is fixed thereto by an adhesive or the like. The connector 56 attached to the proximal end of the guide tube assembly 50 is fixedly secured to the fitting 13 by a fastener member 59. The cylindrical fastener member 59 has an internally-threaded portion 59a on an inner peripheral surface thereof, and has a radially inwardly-directed flange 59b at one end thereof. By threading the threaded portion 59a of the fastener member 59 on the threaded portion 13b of the fitting 13, one end portion of the connector 56 is inserted into the greater-diameter portion 13c' of the central bore 13 of the fitting 13, so that the flange 56b of the connector 56 is held between the flange 59b of the fastener member 59 and the inner end of the fitting 13.

In the endoscope of the above construction, the forceps is inserted into the inlet 15 of the body 10, and is passed through the guide channel 50a and the outlet 35, and is directed toward the body cavity. The operator, while observing the interior of the body cavity, effects a remote control with respect to the proximal end of the forceps, thereby causing the distal end of the forceps to carry out a predetermined operation or treatment with respect to the inner surface of the body cavity.

In the guide tube assembly 50 of the above construction, the resin tube 51 has the spiral grooves 51a and 51b, and the peripheral wall of the resin tube 51 has a corrugated cross-section. Therefore, the resin tube 51 is highly flexible in the direction of bending of the guide tube assembly 50. The reinforcement coil 52 is also highly flexible so that it can be easily bent longitudinally. Further, the yarns 53a per se are flexible, and besides the yarns 53a are displaced with respect to one another when the braid tube 53 is bent. Thus, the braid tube 53 is highly flexible. Therefore, the guide tube assembly 50 is highly flexible, and particularly when the bendable portion 21 is to be bent, the guide tube assembly 50 does not offer a large resistance to such bending, thus allowing an easy bending of the bendable portion 21.

The reinforcement coil 52 reinforces the resin tube 51 so that the resin tube 51 may not be crushed or flattened when the guide tube assembly 50 is bent. The braid tube 53 prevents the reinforcement coil 52 from becoming disengaged from the spiral grooves 51a of the resin tube 51.

In the guide tube assembly 50, the braid tube 53 is made of the yarns 53a having very low expansion properties. Therefore, in order that the braid tube 53 can be expanded longitudinally, the above intersection angle $\theta$ must be reduced so as to reduce the diameter of the braid tube 53. However, as described above, the reduction of the diameter of the braid tube 53 and hence the longitudinal expansion of the braid tube 53 are prevented by the reinforcement coil 52. Therefore, the resin tube 51 which is fixed at its opposite ends with respect to the braid tube 53 is also prevented by the braid tube 53 from being longitudinally expanded even if the guide tube assembly 50 is repeatedly bent.

To summarize, the guide tube assembly 50 maintains a high flexibility in the bendable direction, and also is prevented from being subjected to an age expansion due to a repeated bending of the bendable portion 21.

Since the longitudinal expansion of the guide tube assembly 50 is prohibited as described above, the guide tube assembly 50 will not be loosened within the endoscope, and therefore the forceps can be smoothly passed through the guide channel 50a, and the inner peripheral surface of the resin tube 51 can be prevented from damage.

Figure 5:
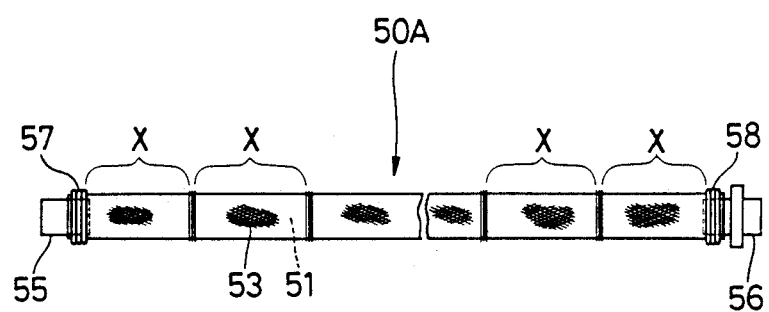
FIG. 5 is a front-elevational view of a modified guide tube assembly.

FIG. 5 shows a modified guide tube assembly 50A of the present invention. Basically, the guide tube assembly 50A is similar to the guide tube assembly 50 shown in FIGS. 1 to 4, and therefore corresponding parts are denoted respectively by the same reference numerals as in the preceding embodiment, and a detailed description of such corresponding parts is omitted here. Opposite ends of a resin tube 51 are fixed respectively to opposite ends of a braid tube 53 through respective connectors 55 and 56. The resin tube 51 and the braid tube 53 are further fixed to each other intermediate their opposite ends by straps 60 which are tied around the braid tube 53 and are spaced from one another along the length of the braid tube 53 at predetermined intervals. With this arrangement, the guide tube assembly 50A is divided into a plurality of sections or regions X by the straps 60. The straps 60 may be replaced by an adhesive which is applied between the resin tube 51 and the braid tube at predetermined intervals.

When the inner surface of the resin tube is urged by the forceps by a frictional contact therebetween at that portion (for example, corresponding to the bendable portion 21) of the guide tube assembly 50A which is bent to a greater extent, the resin tube 51 is longitudinally expanded and contracted only at that section X including said that portion of the guide tube assembly 50A. More specifically, the resin tube 51 is expanded forwardly of the front end of the forceps, and is contracted rearwardly of the front end of the forceps. However, the amounts of such expansion and contraction are limited by the resistance offered by that portion of the resin tube 51 corresponding to said that section X. The other sections X are not influenced by the above frictional contact of the forceps.

The present invention is not to be restricted to the above embodiments, and many modifications can be made. For example, the reinforcement coil 52 may not be helically wound around the resin tube 51 over the entire length thereof, and may be wound around only that portion of the resin tube 51 corresponding to the bendable portion 21.

The present invention is applicable to an endoscope for an industrial use. In this case, the guide tube assembly serves to guide a measuring instrument or the like. The present invention is also applicable to an electronic endoscope connectable to a television.

What is claimed is:

1. An endoscope comprising:
    (a) a body having an inlet for an elongated treatment instrument;
    (b) a flexible insertion tube extending from said body;
    (c) a rigid member mounted on a distal end of said insertion tube remote from said body, said rigid member having an outlet for said treatment instrument; and (d) a guide tube assembly for guiding said treatment instrument, said guide tube assembly being received in said body and said insertion tube and comprising (i) a resin tube whose internal bore serves as a guide channel for the passage of said treatment instrument therethrough, said guide channel interconnecting said inlet of said body and said outlet of said rigid member, said resin tube having a spiral groove formed in an outer peripheral surface thereof, (ii) a reinforcement coil received in said spiral groove in said resin tube, and (iii) a braid tube woven of yarns having low expansion properties, said braid tube being covering said resin tube generally over an entire length of said resin tube, and opposite ends of said braid tube being fixed to opposite ends of said resin tube, respectively.

2. An endoscope according to claim 1, in which the inner peripheral surface of said braid tube of said guide tube assembly is held in contact with said reinforcement coil.

3. An endoscope according to claim 1, in which said yarns constituting said braid tube of said guide tube assembly are made of aromatic polyamide.

4. An endoscope according to claim 1, in which said resin tube and said braid tube are fixed to each other intermediate the opposite ends of said guide tube assembly.

5. An endoscope according to claim 1, in which said guide tube assembly has a pair of proximal and distal tubular connectors provided at proximal and distal ends thereof, respectively, the opposite ends of said resin tube being fixedly secured to inner peripheral surfaces of said pair of connectors, respectively, the opposite ends of said braid tube being fixedly secured to outer peripheral surfaces of said pair of connectors, respectively, said distal connector being fitted in and fixed to said outlet of said rigid member, and said proximal connector being fitted in and fixed to said inlet of said body.

6. An endoscope according to claim 5, in which internally-threaded portions are formed on the inner peripheral surfaces of said pair of connectors, respectively, the opposite ends of said resin tube being threaded into said internally-threaded portions, respectively.

* * * * *